United States Patent [19]

Katsuda et al.

[11] Patent Number: 4,693,868
[45] Date of Patent: Sep. 15, 1987

[54] THERMAL FUMIGATOR FOR DRUGS

[75] Inventors: Yoshio Katsuda, Nishinomiya; Sadao Yoshinaga, Ichikawa; Hiroyoshi Mashine, Souka, all of Japan

[73] Assignee: Dainihon Jochugiku Co., Ltd., Japan

[21] Appl. No.: 611,037

[22] PCT Filed: Sep. 30, 1983

[86] PCT No.: PCT/JP83/00323

§ 371 Date: May 9, 1984

§ 102(e) Date: May 9, 1984

[87] PCT Pub. No.: WO84/01264

PCT Pub. Date: Apr. 12, 1984

[30] Foreign Application Priority Data

| Sep. 30, 1982 | [JP] | Japan | 57-148579[U] |
| Sep. 30, 1982 | [JP] | Japan | 57-148580[U] |
| Sep. 30, 1982 | [JP] | Japan | 57-148581[U] |
| Oct. 4, 1982 | [JP] | Japan | 57-174295 |
| Oct. 8, 1982 | [JP] | Japan | 57-153100[U] |
| Oct. 8, 1982 | [JP] | Japan | 57-177050 |
| Nov. 8, 1982 | [JP] | Japan | 57-169122[U] |
| Nov. 8, 1982 | [JP] | Japan | 57-169123[U] |
| Jan. 6, 1983 | [JP] | Japan | 58-373[U] |
| Jan. 6, 1983 | [JP] | Japan | 58-374[U] |
| Feb. 16, 1983 | [JP] | Japan | 58-20971[U] |
| Sep. 26, 1983 | [JP] | Japan | 58-177647 |

[51] Int. Cl.$^4$ ............................................. A61L 9/04
[52] U.S. Cl. ............................ 422/124; 422/305; 422/306
[58] Field of Search .............. 423/247; 422/177, 211, 422/292, 297, 298, 299, 305, 306, 307, 28, 4, 180, 124, 125, 123

[56] References Cited

U.S. PATENT DOCUMENTS

| 247,480 | 9/1881 | Carpenter | 422/125 |
| 3,043,245 | 7/1962 | Herbert et al. | 422/177 |
| 3,923,458 | 12/1975 | Moran | 422/125 |
| 4,163,038 | 7/1979 | Nishimura et al. | 422/36 |
| 4,171,340 | 10/1979 | Nishimura et al. | 422/36 |
| 4,458,662 | 7/1984 | Barnett | 423/247 |

FOREIGN PATENT DOCUMENTS 432047 1/1968 Japan .
506912 2/1975 Japan .

Primary Examiner—David L. Lacey
Attorney, Agent, or Firm—Parkhurst & Oliff

[57] ABSTRACT

A thermal fumigator is disclosed which vaporizes a drug in order to fumigate a space. The drug is vaporized by heat generated when the vapors of a volatile fuel come in contact with a metal catalyst. The fumigator includes a fuel container, a metal catalyst and a compressed mat, impregnated with a drug, which are held at fixed distances from each other for maximum efficiency.

18 Claims, 11 Drawing Figures

FIG. 6
FIG. 7
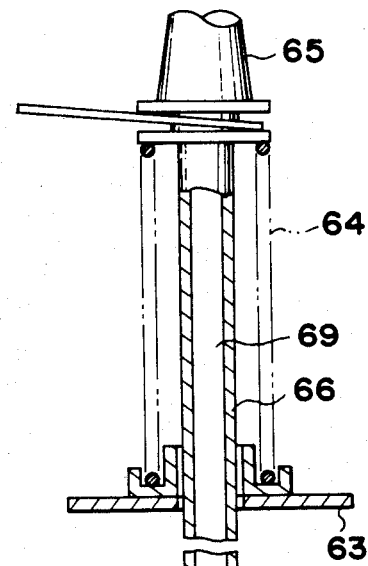
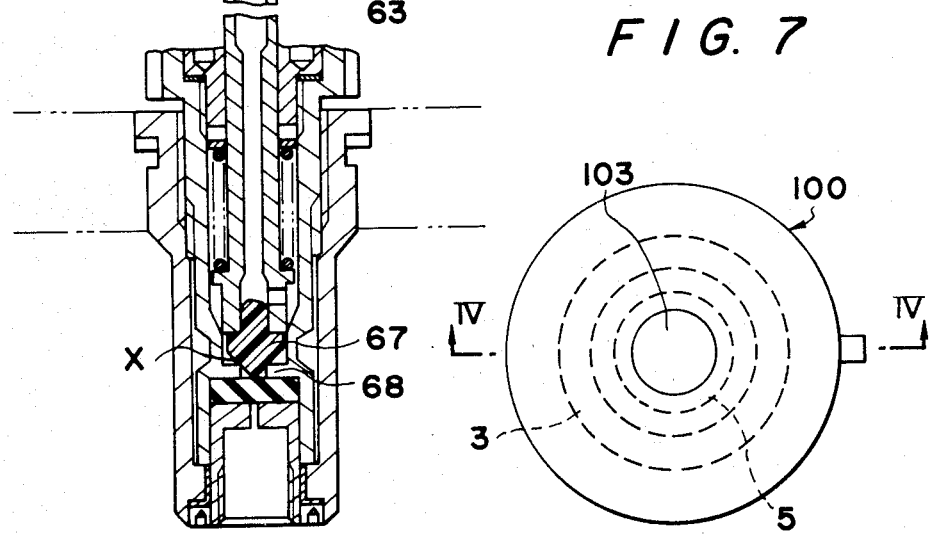

THERMAL FUMIGATOR FOR DRUGS

BACKGROUND OF THE INVENTION

This invention relates to a thermal fumigator for drugs such as insecticides, fungicides, room aromatizers, and deodarants.

DESCRIPTION OF PRIOR ART

Devices such as electric mosquito killers which fumigate a room interior by heating a mat impregnated with drugs such as insecticides thereby releasing the drugs in fume form from the mat, have been known to the art. Since these devices utilize electricity as a heat source for heating the mat, they inevitably suffer from complicated construction. The use of electricity entails a disadvantage that the devices require electric cables for their power sources and, consequently, their uses are limited to those places which are provided with electric power.

Although the practice of keeping mosquito coils burning outdoors for protection against insect bites has been popular, unfortunately this practice is not necessarily safe because it inevitably requires the continuous presence of fire at the leading ends of such mosquito coils until the desired protection becomes no longer necessary.

A liquefied gas fumigator designed to operate on the principle of the pocket warmer has also been known in the art. In this fumigator, the principle of the pocket warmer (in which the fuel such as benzene is converted into a heat-carrying vapor by combustion aided by a wad of asbestos impregnated with a catalyst such as platinum or palladium) is diverted without any alteration to fumigation of an insecticide. Although this principle is completely satisfactory for the purpose of retaining warmth, it is not fit for an insecticide fumigator which must maintain accurate temperature control.

This known method suffers from the disadvantage that it fails to attain the object of retaining a constant temperature level because:

(1) a platinum impregnated wad provides no homogeneous catalytic action and (2) a supply of oxygen is not uniform enough to permit formation of a uniform mixture of the fuel with oxygen.

SUMMARY OF THE INVENTION

This invention originated in the determination to eliminate the aforementioned drawbacks inherent in the conventional thermal fumigators for drugs and preclude the danger due to the use of fire. It provides a catalyst-heating type thermal fumigator for drugs which utilizes as its heat source the reaction heat caused when a volatile fuel (such as alcohol) or a liquefied gas fuel (such as liquefied petroleum gas or dimethyl ether) is brought into contact with a catalyst of platinum or palladium in air. It is simple in construction and does not need a cable for power source connection and imposes no limitation on the selection of places of use.

The thermal fumigator for drugs (hereinafter referred to as "thermal fumigator") of the present invention is characterized by a case having a receptable for a volatile fuel or liquefied gas fuel, a metal catalyst disposed above the aforementioned receptacle across a proper intervening space, and a heat radiating plate disposed above the aforementioned metal catalyst across said space and adapted to permit thermal release of a drug. It is further characterized by a passage in the aforementioned case for supply of air and release of combustion gas.

In another aspect, the thermal fumigator of this invention is characterized by a case having a container for sealing a liquefied gas, a nozzle communicated via a valve with the aforementioned container, a metal catalyst disposed at a position where the gas escaping from the nozzle collides with the metal catalyst, and a heat radiating plate disposed near the aforementioned catalyst and adapted to permit thermal release of a drug. Also provided in the case is a passage for supply of air and release of combustion gas and a control means for regulating the opening and closing of the aforementioned valve.

The thermal fumigator of the present invention accomplishes the heretofore unattainable uniform retention of effective temperature by interposing a fixed space between the fuel container and the metal catalyst to ensure thorough mixture of the fuel gas with oxygen and further interposing a fixed space between the metal catalyst and the heat radiating plate for release of the drug to produce efficient progress of the convectional flow of the combustion gas.

In a preferred embodiment of this invention, the thermal fumigator may be of a construction such that the space formed above the fuel receptacle and the space formed above the metal catalyst to embrace therein the heat radiating plate for thermal release of the drug may be partitioned from each other with a thermally insulating plate.

The thermal fumigator may be of a construction such that a member for retaining the metal catalyst in position and the heat radiating plate for thermal release of the drug may be interconnected to each other with a common metal member.

Further, the thermal fumigator may be of a construction such that the fuel receptacle may be a container of the type capable of keeping its content replenished or of the type capable of keeping its content sealed therein so as to carry thereon or receive and retain therein a volatile solid fuel, a volatile liquid fuel, or a liquefied gas fuel.

BRIEF DESCRIPTION OF THE DRAWINGS

FIG. 6 is an enlarged view of a valve control means B in the thermal fumigator.

FIG. 7 is a plan view of another thermal fumigator of this invention.

DESCRIPTION OF A PREFERRED EMBODIMENT OF THIS INVENTION

Figure 1:
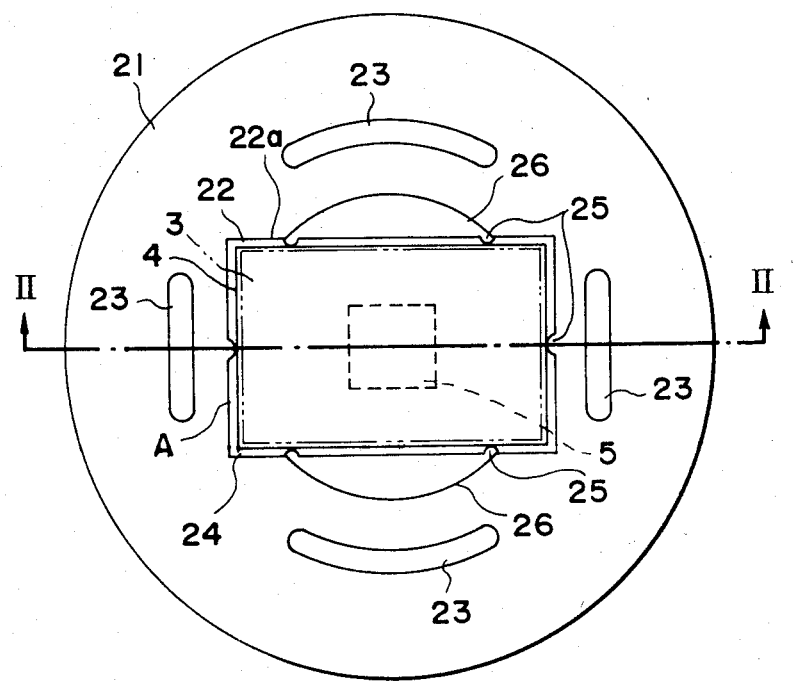
FIG. 1 is a plan view illustrating a typical thermal fumigator of the present invention.
Figure 2:
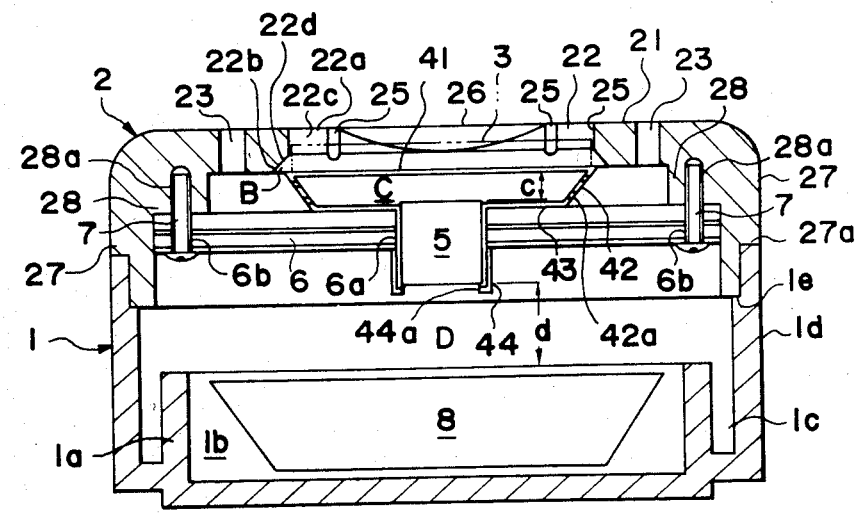
FIG. 2 is a cross section taken along the line II—II of FIG. 1.

One typical thermal fumigator of this invention is illustrated in FIG. 1 and FIG. 2. In the figures, 1 denotes a case body of the shape of a blind tube, with the interior thereof divided into a fuel receptacle 1b and a water reservoir 1c with an internally formed cylindrical inner wall 1a. A lateral wall (outer wall) 1d of the case body 1 extends upwardly above the aforementioned inner wall 1a. On the inner side at the upper extremity of the extended portion of the outer wall 1d, a stepped part 1e is formed throughout the entire circumference of the fumigator case to be fitted by a case lid 2.

The case lid 2 is a member comprising a circular top plate 21 and a cylindrical lateral wall 27 and having a cross section substantially of the letter "U" shape. The top plate 21 is provided substantially at the center thereof with a rectangular opening 22 and outside the edges of the opening 22 with air vents 23. The opening 22 on an uppper side 22a of the top plate 21 has a rectangular shape similar to and slightly larger than an insecticidal mat 3 which is set in position within the termal fumigator. On its lower side 22b it has a rectangular shape similar to and slightly larger than the upper end of a heat radiating member 4 serving to support thereon the insecticidal mat 3. The inner wall defining the opening 22, relative to the direction in which the opening 22 is bored in the case lid 2, is divided by a plane passing near the middle of the thickness of the top plate 21 into an upper vertical wall 22c and a lower, downwardly inclined wall 22d. A gap A (see FIG. 1) to be formed between the insecticidal mat 3 and the vertical wall 22c of the opening 22 and a gap B (see FIG. 2) to be formed between the heat radiating member 4 and the inclined wall 22d of the opening 22, allows an air escape gap 24 serving as a free air passage between the interior and the exterior of the case lid, to be secured intact even after the insecticidal mat 3 has been set in position on the heat radiating member 4. Inward protuberances 25 are formed on the wall of the opening 22. These protuberances 25 enable the insecticidal mat 3 to be accurately set at the center of the opening 22 and rectify the flow of air through the air escape gap 24 between the insecticidal mat 3 and the wall of the opening 22. Depressions 26 in the upper surface of the top plate 21 are smoothly inclined downwardly from the periphery to the center of the top plate 21. They terminate along the pair of major sides of the opening 22. These depressions 26 are intended for the purpose of enhancing the ease with which the insecticidal mat 3 is (a) inserted into the opening 22 and mounted on the heat radiating member 4 or (b) from the thermal fumigator.

On the inner side of the portion at which the top plate 21 and the lateral wall 27 of the case lid 2 adjoin each other, a shoulder part 28 is formed along the entire circumference of the lateral wall 27. This shoulder 28 is intended for the purpose of steadily holding a support member 6 which supports in position a catalyst 5, and the heat radiating member 4. Holes 28 for screws are used for fastening the support member. A stepped part 27a is formed along the entire periphery in the lower portion of the lateral wall 27. This stepped part 27a is shaped so as to be tightly fitted into another stepped part 1e which is formed on the outer wall 1d of the case body 1. The case lid 2 is enabled to cover the upper side of the case body 1 and complete a whole case by causing the stepped part 27a of the lateral wall to be snugly fitted into the stepped part 1e of the outer wall of the case body 1. Matching threads may be cut in advance on the lateral surfaces of the case 2 and the inner wall of the case body so that the case body 1 and the case lid 2 will be helically joined with each other.

The insecticidal mat 3 is a rectangular plate of compressed fibers impregnated with an insecticidally active drug solution. This rectangular shape is not critical to the function to be fulfilled by the insecticidal mat 3. This mat 3 may be in any shape if it can be inserted into the opening 22 of the case lid 2.

Figure 3A:
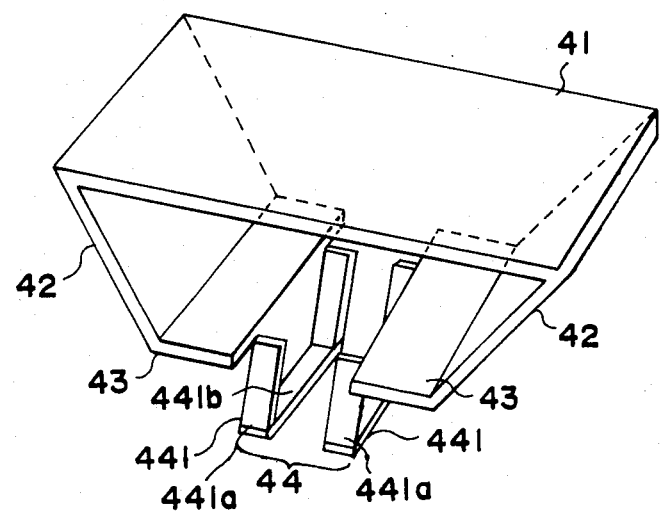
FIGS. 3(A) and (B) are each a perspective view of a typical heat radiating member of this invention.

The heat radiating member 4 is intended for the purpose of supporting thereon the insecticidal mat 3 and applying heat thereto and enabling the mat 3 to release the insecticidally active drug in fumes. This heat radiating member 4 is made of a heat radiating plate joined with a catalyst retaining part. An enlarged perspective view of this heat radiating member is given in FIG. 3(A).

The heat radiating member 4 comprises; a horizontal heat radiating plate 41 adapted to support thereon the insecticidal mat 3 and apply heat thereto, lateral parts 42 extending from the opposite ends of the heat radiating plate 41 downward toward each other at a slight incline, lower plates 43 extending from the lower ends of the aforementioned lateral parts 42 toward each other and parallel to the aforementioned heat radiating plate 41, and a catalyst retaining part 44 formed by a pair of catalyst retaining pieces 441 extended downwardly from the opposed edges of the lower plates 43. The opposed edges 441a of each of the catalyst retaining pieces 441 are bent so as to protrude inwardly toward the center of the heat radiating plate and the lower edge 441b thereof is similarly bent so as to protrude inwardly toward the center. A catalyst 5 is held in position by a catalyst support member which includes the inwardly extended lateral edges 441a and lower edges 441b. The heat radiating member 4 is integrally formed with a metal plate having excellent thermal conductivity.

Optionally, the lateral parts 42 may be provided with air passages holes 42a through which air will be supplied to the catalyst and the combustion gas emanating from the catalyst 5 will be discharged out of the heat radiating member 4. The heat radiating plate 41 may be porous, so that part of the combustion gas emanating from the monolithic catalyst 5 will find outlet through the bores of the heat radiating plate 41 to accelerate the oxidation reaction of the fuel by the monolithic catalyst 5 and refrain from interfering with the thermal convection of the combustion gas. This provision of bores of the heat radiating plate 41 is not critical to the function of the heat radiating member 4.

Between the heat radiating plate 41 and the lower plates 43, there is embraced a space C having a height fixed by the lateral parts 42. Owing to the space C thus formed, the catalyst 5 is prevented from coming into direct contact with the heat radiating plate 41. The distance of the space C, namely the interval separating catalyst and the heat radiating plate (the part for heating the drug) from each other (indicated as C cm in FIG. 2) is desired to be at least 0.2 cm and more desirably to fall in the range of 0.3 cm to 3.0 cm. If the catalyst and the heat radiating plate are held in mutual contact or if they are separated by too small an interval (C 0.2 cm), the desired convection of the combustion gas and the oxidation reaction of the fuel are obstructed and the heat radiating plate fails to apply ample heating. It is only when the catalyst and the proper plate are separated from each other by a catalyst support member which includes an interval of at least 0.2 cm that the heat radiating plate can be most efficiently heated to a desired elevated temperature by the convection of the combustion gas emanating from the catalyst.

Figure 3B:
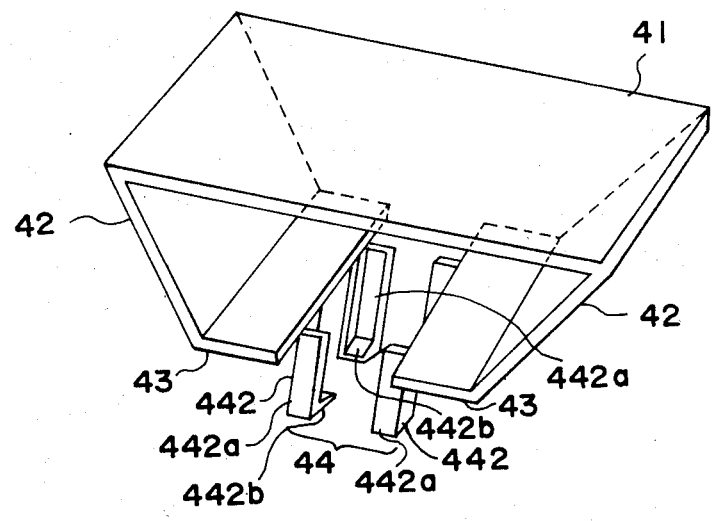

One modification of the heat radiating member is illustrated in FIG. 3(B). In substantially the same construction as the heat radiating plate so far described, this modified heat radiating member comprises heat radiating plate 41, lateral plates 42, lower parts 43, and four slender leg parts 442 extended downwardly from the inner edges of the lower parts 42. Each of the leg parts 442 comprises a slender lateral wall 442a having a cross section in the shape of the letter L and a horizontal bottom part 442b extended inwardly from the lower end of the lateral wall 442a and adapted to support the catalyst position. Two such leg parts 442 are attached as opposed to each other in the stated position of each of the aforementioned lower parts 43. The total of four leg parts 442 collectively constitutes a catalyst retaining part 44.

This modified heat radiating member has the advantage that the conduction of heat from the catalyst 5 to the heat radiating plate 41 is carried out without any obstacle and the heat radiating member 4 itself enjoys reduction in weight because the catalyst retaining part 44 if formed of four slender leg parts 442.

The monolithic catalyst 5 is formed in an angular shape fit for snug insertion in the angular pillar part 44 of the aforementioned heat radiating plate 4. It comprises a ceramic carrier in a honeycomb structure and a catalytically active metal such as platinum or palladium deposited on the ceramic carrier. The catalyst 5 to be used in this invention is not limited to this description as a matter of course. It may be in the form of an aggregate of beads or a mass of wool, etc., as occasion demands.

A thermally insulating plate support member 6 serving to secure the heat radiating member 4 and the catalyst 5 to the case lid 2. It is a circular plate having a diameter such that the periphery thereof can intimately abut the inner surface of the lateral wall 27 of the lid 2. The thermally insulating plate support member 6 is provided near the center thereof with a hollow part 6a capable of receiving insertion of the angular pillar part 44 of the aforementioned heat radiating member 4. The thermally insulating plate support member 6 is further provided at suitable positions with holes 6b for insertion of setscrews 7 which are fastened to the lid 2. The holes 6b for the insertion of these setscrews are bored as accurately aligned with the screw holes 28a which are formed in the shoulder 28 of the lid 2. Although the material of the thermally insulating plate support member 6 is not specifically limited, it is either impervious to air or slightly previous to air and should be heat resistant and pevent passage of heat. It is desirably formed of glass fibers, for example.

A fuel container 8 which is mounted in the fuel receptacle 1b is open at the top and is adapted to be filled with a volatile fuel. The fuel container 8 filled with the fuel is stowed in the fuel receptacle 1b of the case body 1. Between the fuel container 8 and the catalyst 5, a space D having a fixed height is retained.

The fuel to be used in the thermal fumigator illustrated in FIG. 1 and FIG. 2 is required to possess volatility and induce an exothermal reaction with the aforementioned catalyst. Exemplary fuels for fulfilling this requirement are alcohols. Methanol or ethanol are preferred choices. Other fuels which are effectively usable herein are liquid alcohols, carboxyvinyl polymer, copolymer of maleic anhydride with isobutylene, copolymers of vinyl alcohols with acrylic acid, alcohols gelled with starch derivatives, and solid fuel having alcohols as main components.

In the thermal fumigator described above with referenced to FIG. 1 and FIG. 2, the insecticidal mat 3 is inserted into the opening 22 of the case lid 2 and set in position on the heat radiating plate 41 of the heat radiating member 4. The alcohol fuel rising in fumes from the fuel container 8 fills up the space D and then ascends through the catalyst 5 disposed above the fuel container 8. During the passage through the catalyst, the fuel alcohol is oxidized by the catalyst of platinum or palladium. The resultant combustion gas is discharged from the catalyst 5. The combustion gas continues to rise, fills up the space C, finds its way through the air vents 42a, flows out through the gap B and the gap A and passes into the ambient air. The heat of the reaction generated by the oxidation of the alcohol fuel of the catalyst 5 is transferred by the convection flow of the combustion gas to the heat radiating plate 41 of the heat radiating member 4 situated above the cataylst 5 to cause an elevation of the temperature of the plate 41. Separately, the heat of the reaction originating in the catalyst is transferred by conduction from the lower parts 43 through the lateral plates 42 to the heat radiating plate 41. Thus, the temperature of the heat radiating plate 41 is uniformly elevated. As the plate 41 has its temperature so elevated, the insecticidal mat 3 mounted thereon is uniformly heated. Consequently, the insecticidally active component contained in the insecticidal mat 3 is diffused in fumes into the ambient air through the opening 22 of the case lid 2. Meanwhile, the air indispensable to the oxidation reaction of the alcohol fuel in the catalyst 5 flows in through the air vents 23 formed on the top plate 21 of the case lid 2, passes through the air holes 42a of the lateral plates 42 and reaches the catalyst 5, its destination. Part of the air thus necessary for the oxidation reaction in the catalyst 5 is separtely supplied through the gaps A and B to the catalyst 5. The water resulting from the oxidation reaction of the fuel is collected and stored in the water reservoir 1c of the case body 1.

Now, the operation of the modified thermal fumigator of this invention by the use of a liquefied gas as its fuel will be described. This fumigator is characterized by a case having a container for sealing a liquefied gas therein, a nozzle communicating with the aforementioned container via a valve, a metal catalyst disposed at a position at which the gas emanating from the nozzle collides with the metal catalyst, a heat radiating part disposed near the catalyst and adapted to provide heat for vaporization of the drug, a passage for supply of air and release of combustion gas and a control means for regulating the opening and closing of the aforementioned valve.

In one aspect of this modification, the metal catalyst may be disposed above the nozzle across a space of a certain height and the heat radiating member for the thermal release of the drug may be disposed above the metal catalyst across a space of a certain height.

Figures 4, 5:
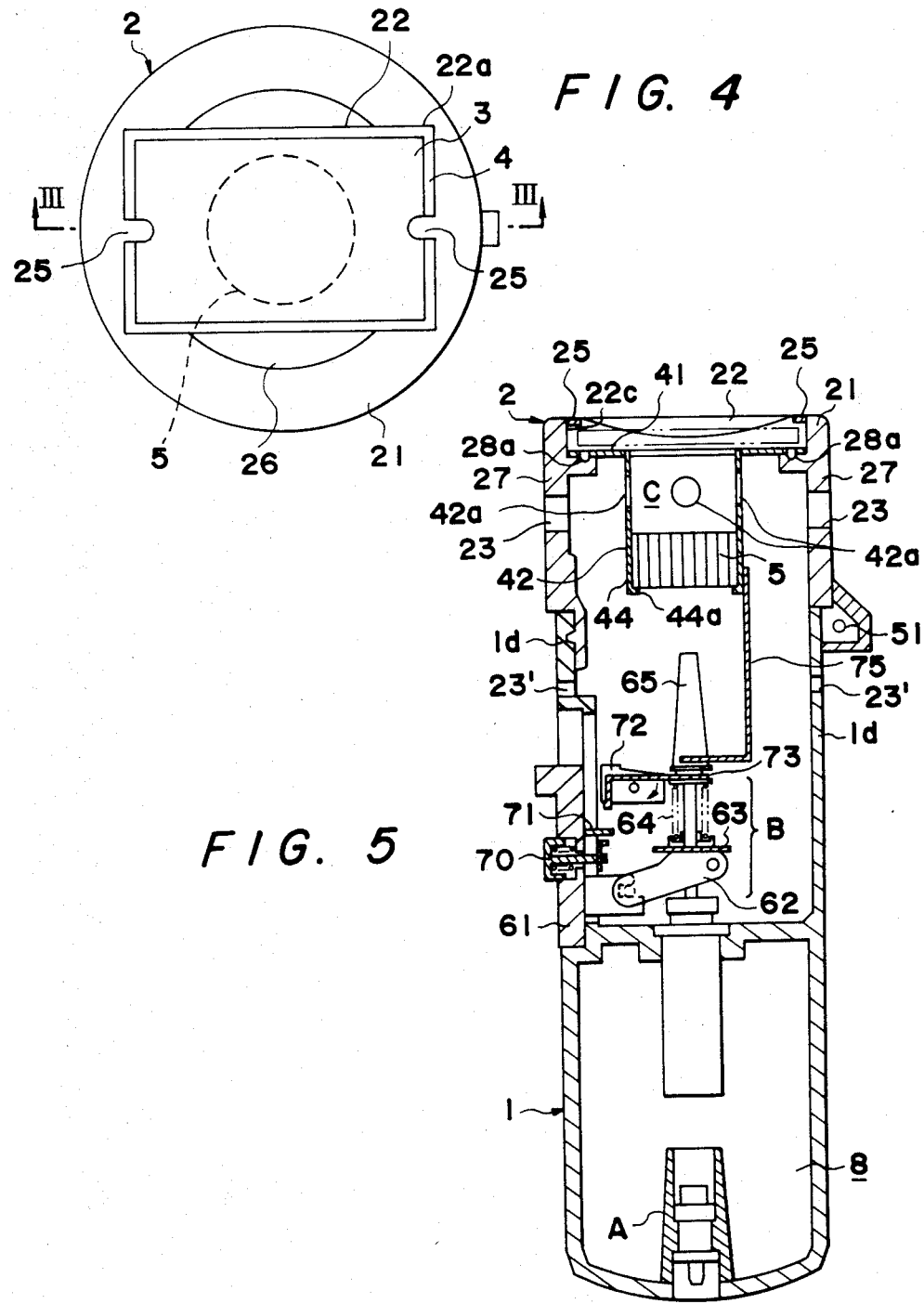
FIG. 4 is a plan view of a thermal fumigator of this invention.
FIG. 5 is a cross section taken along the line III—III of FIG. 4.

FIG. 4 is a plan view illustrating a typical thermal fumigator conforming to the modification described above and FIG. 5 is a cross section taken along the line III—III of FIG. 4. In FIG. 4 and FIG. 5, a blind tubular case body 1 encloses a container 8 which is provided with an injection valve mechanism A for sealing a liquefied gas in the container. The container 8 is partitioned off from the rest of the case body 1 in the middle part of the case body 1. The case body 1 is further provided with air vents 23'.

In the present embodiment, a case lid 2 is a member having a cross section substantially of the shape of letter "U", comprising a circular top plate 21 and a tubular lateral wall 27. The opening 22 on the front side 22a of the top plate has a rectangular shape similar to and slightly larger than the insecticidal mat 3 set in position within the thermal fumigator and also similar to the upper side of the heat radiating member 4 serving to support thereon the insecticidal mat 3. The wall defining the opening 22, relative to the direction in which the opening 22 is bored in the top plate, comprises a vertical surface 22c parallel to the direction of the thickness of the top plate 21. Protuberances 25 formed on the vertical wall 22c of the opening as raised inwardly into the interior of the opening 22. These protuberances 25 are intended for the purpose of allowing the insecticidal mat 3 to be accurately set in position at the center of the opening 22 and preventing it from randomly falling out of position. Depressions 26 in the surface of the top plate 21 are smoothly inclined downwardly in the direction from the periphery to the center of the top plate and terminated along the pair of major sides of the opening 22. These depressions 26 are intended for the purpose of enhancing the ease with which the insecticidal mat 3 is inserted into the opening 22 and mounted on the heat radiating member 4 or removed from the thermal fumigator.

The tubular lateral wall 27 is provided with air vents 23 which permit free flow of air and release of combustion gas.

The case lid 2 is hinged to the case body 1 by means of a fulcrum 51 formed on the lateral wall 1d of the case body at the lowermost part of the lateral wall 27 of the case lid and can be opened and closed freely relative to the case body 1.

On the rear side of the portion at which the top plate 21 and the lateral wall 27 of the case lid 2 join each other, a shoulder part 28 is formed along the entire periphery of the lateral wall 27. This shoulder part 28 is intended for the purpose of fastening in position the catalyst 5 (which will be described more fully below) and the heat radiating member 4 receiving and retaining therein the catalyst 5. Holes in the lateral wall 27 are for insertion of screws serving to fasten the heat radiating member 4.

The insecticidal mat 3 is a rectangular plate of compressed fibers impregnated with an insecticidally active component solution. This rectangular shape is not critical to the function to be fulfilled by the insecticidal mat. This mat 3 may be in any desired shape insofar as it can be inserted into the opening 22 of the case lid 2.

The heat radiating member 4 supports the insecticidal mat 3 and applies heat thereto in order that the mat 3 may release the insecticidal component in fumes. The heat radiating member 4 comprises a heat radiating plate 41 adapted to support thereon the insecticidal mat 3 and apply heat thereto, a lateral tubular part 42 extended downwardly from substantially the center of the heat radiating plate 41, and a tubular member 44 extended further downwardly from the lateral tubular member and adapted to retain the catalyst therein. All the component members of the heat radiating member 4 are made of a metal material. The lateral tubular member 42 is provided with air passage holes 42a through which the combustion gas emanating from the catalyst can be released into the ambient air. The heat radiating plate 41 may be porous. The bores of the heat radiating plate 41 will permit escape of part of the combustion gas being issued from the monolithic catalyst 5. They advantageously serve as means for promoting the oxidation reaction of the fuel in the monolithic catalyst 5 and enabling the convection of the combustion gas to proceed without any obstacle. The provision of these bores is not critical to the function of the heat radiating plate. The tubular member 44 is provided at the lower end thereof with a flange 44a protruding inwardly into the interior of the tubular member 44, so that when the monolithic catalyst 5 is stowed in this tubular member 44, it may be safely retained on the flange 44a. Between the heat radiating member 4 and the catalyst 5, there is formed a space C having a fixed height. This space C serves to keep the monolithic catalyst 5 separated from the heat radiating plate 41 supporting the insecticidal mat 3 thereon.

The monolithic catalyst 5 is in a tubular shape fit for insertion in the tubular member 44 of the aforementioned heat radiating member 4. It comprises a ceramic carrier of honeycomb structure and a catalytically active metal such as platinum or palladium deposited on the ceramic carrier. The catalyst 5 to be used in this invention is not limited to this particular shape. It may be in the form of an aggregate of beads or in a mass or wad, for example.

It is advantageous to isolate the space above the nozzle from the space above the metal catalyst with a thermally insulating plate to separate the holes for feed air and the holes for release of the combustion gas and concurrently use this thermally insulating plate as a catalyst retaining member.

A container 8 for sealing in a liquefied gas is provided with a nozzle 65 which is communicated with the interior of the container via a valve (FIG. 6). This container 8 is filled with a liquefied gas which serves as the fuel.

As the fuel, any liquefied gas may be used insofar as the gas is capable of causing an oxidation reaction with the aid of the aforementioned catalyst 5. Concrete examples of the liquefied gas satisfying this requirement are liquefied petroleum gas (LPG), dimethyl ether, hexane, benzene, and gases usable for cigarette lighters. The container 8 is provided thereon with valve control means B capable of regulating the opening and closing of the valve X serving to adjust the release of the liquefied gas. This control means B is interlocked with a switch 61 which is provided in the case body so as to control the supply of the liquefied gas to the medium of the catalyst 5 to consequently uniformize the temperature of the heat radiating member 4.

In the thermal fumigator constructed as described above, the insecticidal mat 3 is inserted into the opening 22 of the case lid 2 and then set in position on the heat radiating plate 41 of the heat radiating member 4. The liquefied gas fuel issued from the container 8 and passed through the nozzle and the air admitted through the air vents 23, 23' jointly pass though the catalyst 5 disposed above the container 8. In the catalyst 5, the liquefied gas fuel is oxidized through the catalysts of platinum or palladium and the resultant combustion gas is released from the catalyst 5. This combustion gas further rises to fill up the space C, passes through the air holes 42a formed in the lateral tubular member 42 of the heat radiating member 4, and passes into the ambient air through the air vents 23. The heat of the reaction generated by the oxidation of the liquefied gas fuel in the catalyst 5 is transferred by convection to the heat radiating plate 41 of the heat radiating member 4 disposed above the catalyst to cause an elevation in the temperature of the heat radiating plate 41. The heat of the reaction produced inside the catalyst 5 is also transferred by conduction through the lateral tubular member 42 of the heat radiating member 4 made of a metallic material to the heat radiating plate 41. Consequently, the temperature of the heat radiating plate 41 is made uniform. As the temperature of the heat radiating plate 41 is thus elevated, the insecticidal mat 3 mounted on the heat radiating plate 41 is uniformly heated enough for the insecticidally active component contained in the insecticidal mat 3 to be dispersed in fumes into the ambient air through the opening 22 of the case lid 2. Meanwhile, the air necessary for the oxidation reaction of the liquefied gas fuel in the catalyst is admitted through the air vents 23 formed in the top plate 21 of the case lid 2 and the air holes 23' in the case body and supplied to the catalyst 5.

The operation of the valve control means during actual use of the thermal fumigator of the aforementioned construction will be described.

FIG. 6 is an enlarged view of the valve control means B for use in the thermal fumigator of this invention.

First a stopper 70 is released and then a switch 61 is pushed up to the valve opening position (for release of the gas). Consequently, a swinging plate 62 is actuated to raise a support metal 63 and the support metal 63 thus raised compresses a spring 64. The upwardly energizing force thus exerted by the spring pushes up a movable valve body 66 which is provided with a nozzle 65.

The upward motion of the movable valve body 66 causes separation of a valve member 67 from a stationary valve seat 68 and consequently opens the valve X which is composed of the valve member 67 and the stationary valve seat 68. This opening of the valve enables the liquefied gas to be passed through a guide hole 69 formed in the movable valve body and then released through the nozzle 65.

At this time, the case lid 2 is opened to expose the nozzle 65 and the liquefied gas issuing from the nozzle 65 is ignited with a match or a lighter. Then the case lid 2 is replaced tightly on the case body 1 and the combustion of the liquefied gas is continued for about 10 seconds until the temperature of the catalyst 5 is elevated to a prescribed level.

At this stage, the stopper 70 is pushed to be released of confinement and the switch 61 is pushed up further.

A pushup plate 71 projected from the switch 61 consequently rotates a rotary plate 72 in the direction of the arrow mark and imparts a downward motion to the leading end of a push-down device 73 integrally fastened to the rotary plate 72. The nozzle 65 which is engaged with the leading end of the push down device 73 is moved downwardly to bring the valve member 68 into fast contact with the stationary valve seat 68, thus closing the valve X.

By this closure of the valve X, the release of the liquefied gas through the nozzle 65 is discontinued and the flame of the liquefied gas is extinguished. After this, the switch 61 is moved downwardly and the stopper 70 is locked at the valve opening position. By this locking of the stopper at its valve opening position, the valve X is opened again and the release of the gas through the nozzle 65 is maintained continuously.

Since the catalyst 5 is now retained in its prescribed heated condition, the liquefied gas released through the nozzle 65 is caused to undergo the reaction rapidly and the catalyst 5 is kep heated.

Now to prevent the catalyst 5 from possible overheating, a bimetal 75 is actuated to control the flow volume of the liquefied gas through the valve X. To be specific, if the movable valve body 66 is left standing in its resilient state, it is kept energized upwardly in the position indicated in FIG. 6. Thus, the bimetal 75 is constructed so that the free end thereof may press down the nozzle 65 against the energizing force. The amount of the depression of the nozzle 65, namely the amount of the displacement of the movable valve body 66, depends on the temperature of the catalyst 5 through this bimetal. Consequently, the valve member 67 and the stationary valve seat 68 are caused by the depressing force of the bimetal 75 to vary the extent of the closing of the valve.

As the result, the amount of the liquefied gas to be released through the nozzle 65 is automatically controlled by the temperature of the catalyst 5, with the natural consequence that the reaction temperature in the catalyst 5 is retained at a fixed level. Then the heat of the reaction generated in the catalyst 5 in effect maintains the temperature of the heat radiating plate 41 of the heat radiating member 4 at a uniform level as described above and the insecticidal mat 3 mounted on the heat radiating plate 41 is uniformly heated in order for the insecticidally active component to be released in fumes from the mat 3.

Termination of the use of the thermal fumigator of this invention is accomplished by releasing the stopper of its confinement and subsequently moving the switch 61 downwardly to the valve closing position. This downward motion of the switch 61 causes the swinging plate 62 to be rotated counter-clockwise and, consequently, the support metal 63 engaged in the swinging plate 62 is moved downwardly. By this downward motion of the support metal, the energizing force of the spring 64 exerted in the direction of lifting the nozzle 65 is weakened. Consequently, the nozzle 65 is brought down to settle on the stationary valve seat 68. Thus, the valve X is closed.

The thermal fumigator of this invention, modiifed to operate with the liquefied gas as its fuel, is not limited to the construction illustrated in FIG. 4 and FIG. 5. When desired, a tubular heat radiating part may be disposed along the lateral side of the catalyst 5 and a doughnut-shaped insecticidal mat 3 may be inserted in the heat radiating member. A typical thermal fumigator incorporating such a tubular heat radiating member and consequently using a doughnut-shaped insecticidal mat is illustrated in FIG. 7 and FIG. 8.

Figure 8:
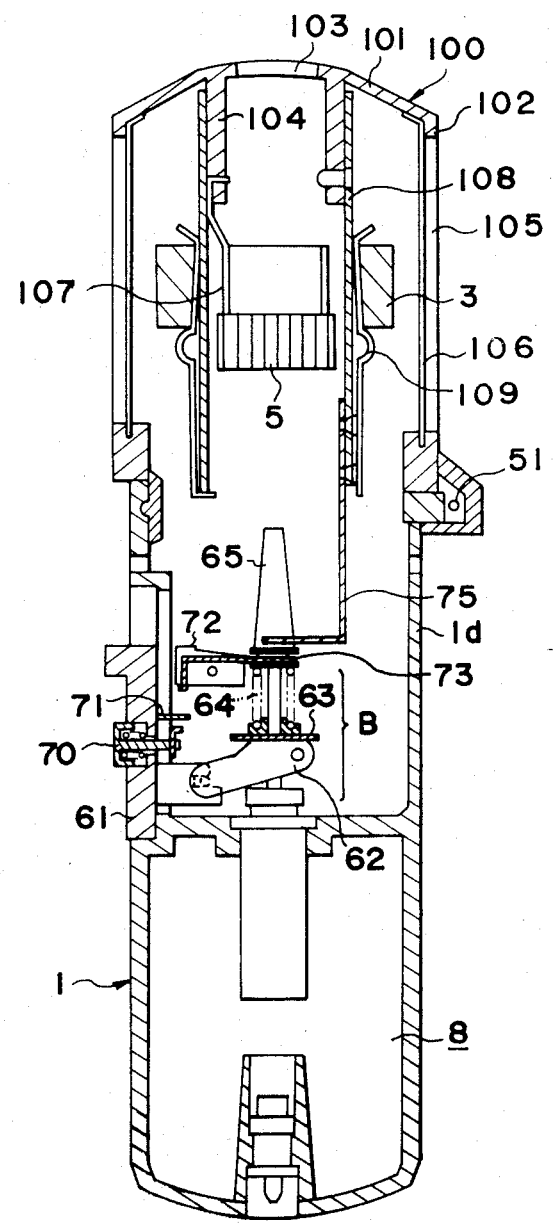
FIG. 8 is a cross section taken along the line IV—IV of FIG. 7.

FIG. 7 is a plan view illustrating another modification of the thermal fumigator using a liquefied gas fuel and FIG. 8 is a cross section taken along the line IV—IV of FIG. 7.

In FIG. 8, a case body 1 has a container 8 for sealing in a liquefied gas. The container 8 communicates with a nozzle 65, with valve control means B disposed therebetween. These parts of the fumigator are identical with the counterparts used in the embodiment illustrated in FIG. 5 and FIG. 6.

A tubular case body 100, comprises a circular top plate 101 incorporating therein a circular opening 103 and a tubular lateral wall 102. The circular opening 103 constitutes a tube in conjunction with an inner tubular lateral wall 104 which forms part of the tubular case body 100. The tubular lateral wall 102 is joined via its lower end to a perforated lateral wall 105. Inside the lateral wall 105, a metal gauze 106 is disposed. Thus, the air is admitted freely into the interior of the tubular case body 100 and the drug released in fumes from the insecticidal mat 3 is discharged freely out of the tubular case body 100 through the lateral wall 105.

The metal catalyst 5 is attached to the inner tubular lateral wall 104 integrally with a heat radiating tube 107. Around the heat radiating tube 107, a metal member 108 is formed, which is further encircled with an insecticidal mat holder 109.

For use in the thermal fumigator constructed as described above, the insecticidal mat 3 is formed in the shape of a doughnut so as to be inserted around the holder 109. Preparatory to the actual use of this fumigator, therefore, the tubular case body is opened by means of a hinge of the fulcrum 51 in order that the insecticidal mat 3 may be inserted around the holder 109.

The liquefied gas released through the nozzle 65 undergoes an oxidation reaction in the catalyst 5 which is heated by the heat reaction, with the result that the heat radiating tube 107 is simultaneously heated. This heat is transferred by conduction through the metal member 108 to the holder 109 spent in uniformly heating the insecticidal mat 3 wrapped around the holder 109. By this heating, the insecticidally active component contained in the mat 3 is liberated in fumes and dispersed from the interior of the tubular case body 100 into the ambient air through the metal gauze 109, and the porous lateral wall 105. The combustion gas which results from the reaction of the liquefied gas fuel in the catalyst 5 is discharged outwardly through the circular opening.

Also in this thermal fumigator, to ensure a uniform heating temperature, the valve for the release of the liquefied gas fuel is controlled with the bimetal 75. The control thus effected is similar to that already described with reference to FIG. 2 and FIG. 3.

On the fumigator constructed as described above, the metal member 108 may be formed in the shape of a pillar having a semicircular cross section and the insecticidal mat holder may be formed in the shpe of a flat plate so that an insecticidal mat formed in the shape of a flat plate will be inserted in position.

In the embodiments so far described, the container 8 for sealing in a liquefied gas are invariably built in the respective case bodies 1 and are provided with an injection valve mechanism A (FIG. 5) capable of freely introducing the liquefied gas into the container 8.

Figure 9:
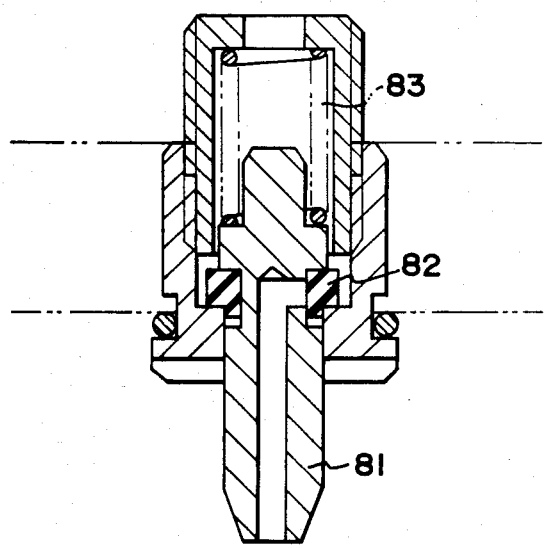
FIG. 9 is an enlarged view of an injection valve mechanism A in the thermal fumigator of this invention.

An enlarged view of the injection valve mechanism A is illustrated in FIG. 9.

This injection valve mechanism A is similar in operating principle to the injection valve mechanisms usually found in gas lighters. To be specific, a movable member 81 is closed with a seal 82 through the agency of the energizing force exerted by a spring 33. During the injection of the liquefied gas, the movable member 81 is moved upwardly (relative to FIG. 9) and, consequently, the seal 82 is also moved upwardly to give rise to an injection hole (open valve). Thus, the liquefied gas is injected through the open valve into the container.

The container 8 for sealing in the liquefied gas is not limited to that which is built in the case body 1. Optionally, a cartridge type liquefied gas container resembling a gas cylinder may be formed separately of the case body 1 and used independently of the case body 1.

The insecticide which can be used by the thermal fumigator of this invention may be any of the various chemical insecticides heretofore adopted for use with, for instance, electric mosquito killers. Typical examples of such insecticides include pyrethroidal insecticides such as 3-allyl-2-methylcyclopenta-2-en4-one-1-yl dl-cis/trans-chrysnthemate (allethrin), 3-allyl-2-methylcyclopenta-2-en-4-one-1-yl d-trans-chrysanthemate, d-3-allyl-2-methylcyclopentan-2-en-4-one-1-yl d-transchrysanthemate, 5-propargyl-2-furylmethyl d-cis/trans-chrysanthemate, 1-ethynyl-2-methylpenta-2-en-1-yl d-cis/trans-chrysanthemate, and 1-ethynyl-2-methylpenta-2-en-1-yl 2,2,3,3-tetramethyl cyclopropane carboxylate. Further, piperonyl butoxide, N-(2-etnylhexyl)-1-isopropyl-4-methylbicyclo-[2,2,2]-octo-5-en-2,3-dicarboxy imide, and octachlorodipropyl ether are typical examples of the pyrethroidal adjuvant which can be used in combination with the aforementioned insecticidal agent. These insecticidal components are incorporated by impregnation in a mat of compressed fibers. The mat may further incorporate therein, besides the insecticidal components mentioned above, an antioxidant such as BHT, BHA, or DBH capable of serving as stabilizers for insecticidal component, dyestuffs which, on exposure to heat, discolor and thereby indicate whether the mat has already been used or not, and perfumes.

In the thermal fumigator of the present invention, an aluminum container filled with a solid chemical capable of being vaporized in fumes fit for the fumigation aimed at by the present invention may be used in the place of the mat impregnated with the insecticidally active component solution. When necessary, the insecide may be substituted with a fungicidal agent, a room aromatizer, or a disinfectant. Any of the various fungicidal agents which possess the volatility of alcohols or dioxines can be used for this purpose.

The thermal fumigator of the present invention is not limited to the constructions illustrated in FIG. 1 through FIG. 8. For example, the air vents are indispensable to the supply of air necessary for the catalytic oxidation reaction of the fuel and to the release of the combustion gas resulting from the oxidation reaction from the interiore of the case body to the ambient air. When necessary, they may be formed in the lateral wall of the case lid or in the outer wall of the case body other than the positions illustrated in such figures. When the air holes for the supply of air are formed in the outer wall of the case body, they are required to be formed in the lowest possible portion of the outer wall of the case body or in the bottom of the case body lest the volatilized fuel should escape through the air holes. Optionally, one air hole may be used simultaneously for the supply of air and for the release of the combustion gas. In this case, the gap formed between the insecticidal mat and the opening may be utilized as the air hole and no other air hole is required.

The shape of the heat radiating plate is not limited to any of the shapes illustrated in the figures. Also the shape of the catalyst is not limited to any of the shapes illustrated in the figures. For example, for the purpose of protecting the catalyst against adhesion of the drug released from the mat, it is advantageous to eliminate the gap formed around the heat radiating plate for release of air and dispose an opening for air discharge at a level far below the heat radiating plate.

It is permissible to stow the catalyst in a receptacle member formed separately of the aforementioned flat shape of heat radiating plate and set in position as pierced through the supporting member. In this case, the receptacle member may comprise vertically opposed retaining pieces adapted to nip the catalyst therebetween. The lateral member may be omitted when the catalyst receptacle member is formed separately of the heat radiating plate as described above. It is nevertheless necessary that the space C of a fixed height should be interposed between the heat radiating plate and the catalyst. The height of this space C, namely the interval separating the catalyst and the heat radiating plate from each other (indicated as C cm in FIG. 2) is required to be at least 0.2 cm and is preferred to fall in the range of from 0.3 cm to 3.0 cm. If the catalyst and the heat radiating plate are held in intimate contact (C=0 cm) or they are separately by too small a distance (C 0.2 cm), ample heating of the heat radiating plate is not obtained because the convection of the combustion gas and the oxidation reaction are prevented from proceeding smoothly in this interval. It is only when the catalyst and the heat radiating plate are separated from each other by a distance of at least 0.2 cm that the heat radiating plate can be most efficiently heated to the elevated temperate by the convection of the heat of the combustion gas emanating from the catalyst.

The shape of the catalyst is not limited to any of the shapes illustrated in the figures. The catalyst may be a monolithic catalyst of the shape of a cylinder.

The container filled with the fuel functions effectively in the thermal fumigator of the present invention if it has an opening in the upper end thereof and the fuel contained therein is efficiently vaporized by the fumigator.

To prohibit return of the water formed during the oxidation reaction to the fuel container, there may be provided inside the fumigator a water receptacle of the shape of a funnel. Otherwise, the part of the fuel container above the neck thereof may be flared upwardly to give rise to a water receptacle of the shape of a funnel.

When a fuel in a gelled form or a solid fuel is adopted, the practice of using the fuel as wrapped in a coarse cloth such as gauze or non-woven fabric, a foamed or porous ceramic or plastic material, or other material which offers no obstruction to the vaporization of the drug proves advantageous for the purpose of preventing the fuel from leaking out of the container or adjusting the amount of the fuel to be vaporized.

The height of the space D, namely the distance, d, separating the fuel and the catalyst from each other is desired to be at least 0.3 cm and preferred to fall in the range of from 0.5 cm to 10.0 cm. If the fuel and the catalyst are held in intimate contact with each other (d=0 cm) or if they are separated from each other by too small a distance (d 0.3 cm), there ensues the disadvantage that the volatilized fuel does not efficiently flow into the catalyst and the fuel is wasted. It is only when the fuel and the catalyst are separated from each other by a distance of at least 0.3 cm that the volatilized fuel is allowed to pass the catalyst smoothly and the oxidation reaction is generated advantageously.

When a volatile solid fuel or volatile liquid fuel is adopted, a fuel receptacle for receiving and retaining the fuel may be constructed so as to serve as a container capable of being replenished with new supply and it may be used in the place of a container specifically designed for the purpose of containing the fuel.

Now, the thermal fumigator of this invention will be described specifically below with reference to working examples:

EXAMPLE 1

5 g of 5-propargyl-3-furylmethyl-d-cis/trans-chrysanthemate, 15 g of N-(2-etnylhexyl)-1-isopropyl-4-methylbicyclo[2,2,2]octo-5-en-2,3-dicarboxy imide, 1.5 g of DBH, and 0.2 g of 1,4-diisopropyl aminoanthraquinone were diluted to a total volume of 100 ml with acetone. A plate of compressed fibers 35×22×2.8 mm was impregnated with 1 ml of the resultant solution. The wet plate was dried in draft to produce an insecticidal mat. This insecticidal mat was used as mounted on the heat radiating plate of the thermal fumigator illustrated in FIG. 1 and FIG. 2.

EXAMPLE 2

6 g of 3-allyl-2-methylcyclopenta-2-en-4-on-1-yl d-cis/trans-chrysanthemate, 4 g of piperonyl butoxide, 2 g of BHT, and 0.3 g of 1,4-dimethyl aminoanthraquinone were dissolved to a total volume of 100 ml with acetone. The same plate of compressed fibers as used in Example 1 was impregnated with 1 ml of the resultant solution and similarly treated to produce an insecticidal mat. This mat was used as mounted on the heat radiating plate of the thermal fumigator illustrated in FIG. 1 and FIG. 2.

EXAMPLE 3

A solution was prepared by mixing 10 g of 1-ethynyl-2-methylpenta-2-en-1-yl d-cis/trans-chrysanthemate, 8 g of N-(2-etnylhexyl)-1-isopropyl-4-methylbicyclo [2,2,2] octo-5-en-2,3-dicarboxy imide, 1 g of DBH, 0.8 g of perfume, 0.2 g of 1,4-diisopropyl aminoanthraquinone, and 10 g of odorless kerosene and heating the resultant mixture to faciliate dissolution of solids. The same plate of compressed fibers as used in Example 1 was impregnated with 0.3 g of the solution and similarly treated to produce an insecticidal mat. This mat was used as mounted on the heat radiating plate of the thermal fumigator illustrated in FIG. 1 and FIG. 2. This fumigator was tried on Culex mosquitos and was found to manifest the same effect as that of any commercially available mosquito coil for more than ten hours.

EXAMPLE 4

A ceramic plate 30×20×3 mm was impreganted with 2 ml of ethanol solution of 1 g of dioxine. The wet ceramic plate was used as mounted on the heat radiating plate of the thermal fumigator illustrated in FIG. 1 and FIG. 2 to fumigate the interior of a.room. The numbers of germs in the room before and after the fumigation were compared by the petri dish method using an agar culture medium. The fumigation was found to have decreased the number of germs in the room to less than 1%.

EXAMPLE 5

A gel was prepared by dissolving 1 g of carboxyvinyl polymer (a product marketed under trademark designation of High-bis Waco 104) in 47 g of an ethanol solution containing 5 g of perfume and subsequently adding 2 g of an aqueous 2% triethanol amine solution to the resultant solution. An aluminum container was filled with 20 g of the gel, mounted on the heat radiating plate of the thermal fumigator illustrated in FIG. 1 and FIG. 2, and used as a room aromatizer.

EXAMPLE 6

The same plate of compressed fibers as used in Example 1 was impregnated with 1 ml of an alcohol solution of 0.5 g of alcohol extract of the deodorant principle present in live leaves of a camellia plant of the family Theaceae. It was mounted on the heat radiating plate of the thermal fumigator illustrated in FIG. 1 and FIG. 2 and used in a water closet to test for deodorizing effect. The fumigation resulted in thorough elimination of the offensive odor of the water closet.

Now, the present invention will be described below with reference to tests.

TEST 1

Figure 10:
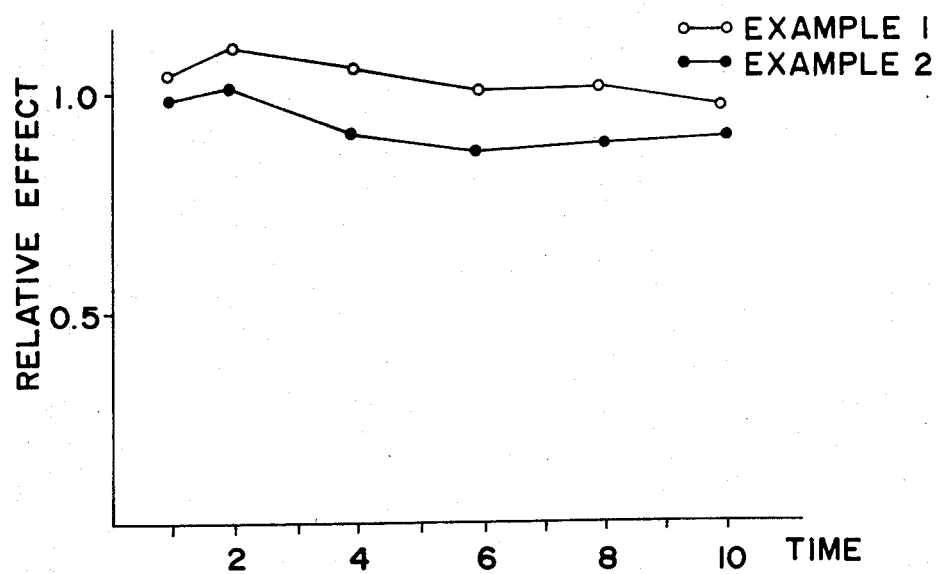
FIG. 10 is a graph showing the results of Test 1.

The thermal fumigator illustrated in FIG. 1 and FIG. 2 was tested for time-course insecticidal effect on Culex mosquitos, with the insecticidal mats obtained in Example 1 and Example 2 each mounted on the heat radiating plate and 25 g of a gel prepared from 90 parts of methanol, 8 parts of ethanol, and 2 parts of a benzylidene derivative of D-sorbit (marketed under trademark designatio of Gelol D) placed in the fuel container. The results were as shown in FIG. 10. The term "relative effect" used in the figure means the change of effect of the fumigant as determined at intervals of one hour and expressed relatively based on the effect determined on elapse of the first hour taken as 1.0. It is clearly noted from FIG. 10 that the insecticidal mats of Example 1 and Example 2 showed high insecticidal effects.

TEST 2

In the thermal fumigator illustrated in FIG. 1 and FIG. 2, the temperature of the heat radiating member 4 was measured while the distance (c cm) between the catalyst 5 and the heat radiating plate 41 and the distance (d cm) between the catalyst 5 and the fuel container 8 filled with the fuel to the upper end of the opening thereof were varied from one test run to another and the gas passage kept open in some test runs and closed in the other test runs. The results were as shown in Table 1. In this test, a solid fuel prepared by thermally dissolving 6 parts of stearic acid in 86 parts of methanol and adding to the resultant solution 8 parts of an aqueous 12.5% sodium hydroxide solution (water:methanol=1 8) was used as the fuel for the fumigator. The temperature of the room in which the test was conducted was kept at 25° C.±1° C.

TABLE 1

| Run No. | Distance (c cm) | Distance (d cm) | Use of gas passage | Average temperature of heat radiating plate* (°C.) |
|---|---|---|---|---|
| 1 | 0.3 | 0 | Yes | 57 |
| 2 | 0.3 | 0.2 | Yes | 67 |
| 3 | 0.3 | 0.3 | Yes | 120 |
| 4 | 0.3 | 0.7 | Yes | 140 |
| 5 | 0.3 | 1.0 | Yes | 140 |
| 6 | 0.3 | 3.0 | Yes | 143 |
| 7 | 0.3 | 5.0 | Yes | 125 |
| 8 | 0.3 | 7.0 | Yes | 100 |
| 9 | 0.3 | 10.0 | Yes | 86 |
| 10 | 0.3 | 12.0 | Yes | 64 |
| 11 | 0 | 1.0 | Yes | 63 |
| 12 | 0.1 | 1.0 | Yes | 72 |
| 13 | 0.2 | 1.0 | Yes | 119 |
| 14 | 0.5 | 1.0 | Yes | 134 |
| 15 | 1.0 | 1.0 | Yes | 113 |
| 16 | 3.0 | 1.0 | Yes | 91 |
| 17 | 4.0 | 1.0 | Yes | 70 |
| 18 | 0.3 | 1.0 | No | 54 |

*The "average temperature" means the average of the temperatures measured hourly between the elapse of the first hour and that of a total of ten hours.

The results of Table 1 indicate the following facts. Comparison of the data of Run No. 1 and those of Run Nos. 2-10 reveals that interposition of a distance between the fuel container (fuel) 8 and the catalyst 5 is necessary and that the temperature of the heat radiating member 4 can be controlled by this distance. Interposition of a distance between the catalyst 5 and the heat radiating plate 41 is also found to be necessary from the comparison of the data of Run No. 5 and Run No. 11. It is shown by comparison of the data of Run No. 5 and those of Run Nos. 11-17 that the size of this distance (c cm) affects the temperature of the heat radiating plate 41. This means that proper combination of the distances, c cm and d cm, permits selection of the temperature of the heat radiating plate 41, depending on the kind of drug and the purpose of fumigation. Comparison of the data of Run No. 4 and those of Run No. 18 reveals that the presence of the gas passage is indispensable for the function of the fumigator. A separate test conducted with respect to the size and number of gas passages formed in the fumigator yielded results which indicate that absolute absence of an elevation in the temperature of the heat radiating plate cannot occur in the presence of a gas passage and that the temperature of the heat radiating plate is fixed when the size of the gas passage is fixed. The data also indicate that the gas passage should not necessarily be formed in the top plate 21 of the case lid 2 and that the effect of the provision of the gas passage is the same when the gas passage is formed in the lateral wall 27 of the case lid 2 and when it is formed in the outer wall 1d of the case body 1.

The data also indicates that the size of the opening in the upper side of the fuel container is variable with the kind of the fuel actually used and the distance between the fuel container and the catalyst, but that the temperature of the heat radiating plate is stable when all these conditions are fixed.

From the results of the test described above, it is noted that for the heat radiating plate in the thermal fumigator of this invention to be efficiently heated with a given heat source, it is imperative to interpose a fixed distance between the fuel container and the catalyst and a fixed distance between the catalyst and the heat radiating plate and further to provide the fumigator with a gas passage and that the other conditions of the fumigator may be suitably varied depending on the object of fumigation, the kinds of drug and fuel, etc.

TEST 3

In the thermal fumigator of FIG. 1 and FIG. 2 and that of FIG. 4 and FIG. 5, the temperatures of the respective heat radiating plates were measured while the kind of volatile fuel used was varied from one run to another. The temperature of the room in which the test was conducted was kept at 25° C.±1° C.

TABLE 2

| Run No. | Volatile Fuel | Average temperature of heat radiating plate* (°C.) |
|---|---|---|
| 1 | Methanol | 141 |
| 2 | Solid fuel made of methanol | 145 |
| 3 | Solid fuel made of methanol and ethanol | 139 |
| 4 | Hexane | 136 |
| 5 | Benzene | 140 |
| 6 | Liquefied petroleum gas | 144 |
| 7 | Dimethyl ether | 140 |
| 8 | Gas for cigarette lighter | 137 |

*The "average temperature" means the average of the temperatures measured hourly between the elapse of the first hour and that of a total of ten hours.

From the results of Test 3 described above, it is noted that in the thermal fumigator of this invetnion, the heat radiating plate obtains its expected temperature insofar as the fuel used therein possesses volatility at normal room temperature and that the variation in the kind of the volatile fuel has no significant difference in this respect.

In Run Nos. 4–8, brief application of heat to the catalyst at the time that the fumigator was put to use served to increase the speed of heat generation.

As is clear from the foregoing description, the thermal fumigator of the present invention accomplishes desired thermal vaporization of a given drug by placing in the fumigator case a volatile fuel or liquefied gas fuel, disposing a catalyst above the fuel across a fixed space, enabling the fuel to undergo an oxidation reaction in the catalyst, allowing the heat of this oxidation reaction to be transferred to a heat radiating plate disposed above the catalyst across a fixed space, and inducing an elevation in the temperature of the heat radiating plate and thereby causing the heat radiating plate to heat the drug deposited thereon. Compared with the conventional drug fumigator which utilizes electricity as the source of heat for the vaporization of a drug, the thermal fumigator of this invention has an advantage that it is simple in construction and is not limited by the place of use. Since the heat radiating plate is uniformly heated by oxidation of the fuel in the presence of the catalyst and, consequently, the drug is vaporized uniformly, the drug incorporated by impregnation in a mat of compressed fibers can be evenly vaporized out of the mat. This fumigator has a salient merit that it provides the uniform retention of available temperature heretofore considered hardly attainable with the conventional fumigator.

Particularly, the thermal fumigator of this invention permits use of a liquefied gas as a fuel capable of generating an oxidation reaction in the presence of a metal catalyst and, accordingly, proves highly convenient in that it enables the liquefied gas to be freely replenished and allows the release of the fuel to be freely regulated. Thus, it enjoys high portability.

What is claimed is:

1. A thermal fumigator for the vaporization of a drug, comprising:
    a fumigator case having a gas passage formed therein;
    a fuel receptacle disposed within a lower portion of said fumigator case;
    a volatile fuel within said fuel receptacle;
    a support member mounted within said fumigator case above said fuel receptacle, said support member comprising a catalyst retaining part and a metal catalyst retained within said catalyst retaining part, said metal catalyst being located at a first predetermined distance above an upper surface of said fuel receptacle, and a heat radiating plate located at a second predetermined distance above said metal catalyst; and
    a mat supported by said heat radiating plate, said mat being impregnated with a vaporizable drug;
    wherein vapors rising from said volatile fuel contact said metal catalyst and generate a heat of reaction which is transferred to said heat radiating plate, whereby said mat is heated and said drug is vaporized.

2. The thermal fumigator of claim 1 further comprising a thermally insulating plate interposed between said fuel receptacle and said heat radiating plate.

3. The thermal fumigator of claim 1 wherein said catalyst retaining part and said heat radiating plate are connected by a metal member.

4. The thermal fumigator of claim 1 further comprising a thermally insulating plate interposed between said fuel receptacle and said heat radiating plate, and a metal member connecting said catalyst retaining part and said heat radiating plate.

5. The thermal fumigator of claim 4 wherein said volatile fuel is a solid and said fuel receptacle receives said solid volatile fuel.

6. The thermal fumigator of claim 4 wherein said volatile fuel is a liquid and said fuel receptacle receives said liquid volatile fuel.

7. The thermal fumigator of claim 4 wherein said volatile fuel is a liquefied gas and said fuel receptacle receives said liquefied gas.

8. The thermal fumigator of claim 1 wherein said volatile fuel is a solid and said fuel receptacle receives said solid volatile fuel.

9. The thermal fumigator of claim 1 wherein said volatile fuel is a liquid and said fuel receptacle receives said liquid volatile fuel.

10. The thermal fumigator of claim 1 wherein said volatile fuel is a liquefied gas and said fuel receptacle receives said liquefied gas.

11. The thermal fumigator of claim 1 wherein said metal catalyst is located such that said first predetermined distance is from 0.3 to 10.0 cm.

12. The thermal fumigator of claim 1 wherein said heat radiating plate is located such that said second predetermined distance is from 0.2 to 3.0 cm.

13. The thermal fumigator of claim 1 wherein said heat radiating plate and said catalyst retaining part are made of metal.

14. The thermal fumigator of claim 1 wherein said heat radiating plate comprises glass fibers.

15. The thermal fumigator of claim 1 wherein said vaporizable drug is an insecticide.

16. The thermal fumigator of claim 1 wherein said volatile fuel is a liquefied gas and said fuel receptacle comprises a container retaining said liquefied gas, said thermal fumigator further comprising a nozzle provided on said container, said nozzle having a valve for releasing said liquefied gas from said container and having an upper end directed at said metal catalyst, and valve control means in said fumigator case for regulating opening and closing of said valve.

17. The thermal fumigator of claim 16 wherein said metal catalyst and an upper surface of said container are separated such that said distance is from 0.3 to 10.0 cm.

18. The thermal fumigator of claim 16 wherein said heat radiating plate is located such that said second predetermined distance is from 0.2 to 3.0 cm.

* * * * *